United States Patent
Sauter

(10) Patent No.: US 6,299,638 B1
(45) Date of Patent: Oct. 9, 2001

(54) METHOD OF ATTACHMENT OF LARGE-BORE AORTIC GRAFT TO AN AORTIC VALVE

(75) Inventor: Joseph A. Sauter, Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/329,506

(22) Filed: Jun. 10, 1999

(51) Int. Cl.[7] ................................. A61F 2/06; A61F 2/24
(52) U.S. Cl. ............................................. 623/1.26; 623/2.1
(58) Field of Search ......................... 623/2.1, 2.11, 623/2.22, 2.24, 2.25, 2.21, 2.38, 2.3, 2.39, 2.4, 2.41

(56) References Cited

U.S. PATENT DOCUMENTS

| | | | |
|---|---|---|---|
| 5,178,633 | * | 1/1993 | Peters ........................................ 623/2 |
| 5,855,603 | * | 1/1999 | Reif ........................................... 623/2 |
| 5,895,419 | * | 4/1999 | Tweden et al. ........................... 623/2 |

* cited by examiner

Primary Examiner—David H. Willse
Assistant Examiner—Alvin Stewart
(74) Attorney, Agent, or Firm—Blossom E. Loo; Timothy L. Scott; Philip S. Lyren

(57) ABSTRACT

An implantable prosthetic heart valve comprising: a valve body, a sewing ring assembly surrounding the valve body and comprising at least a fabric collar and preferably also a stiffening ring, and a tubular vascular graft having a proximal end and a distal end. The proximal end of the graft passes between the fabric collar and the valve body, but not between the stiffening ring and the valve body. The proximal end of the graft is preferably retained by a retaining ring that engages a retaining ring in the downstream end of the fabric sleeve.

19 Claims, 3 Drawing Sheets

METHOD OF ATTACHMENT OF LARGE-BORE AORTIC GRAFT TO AN AORTIC VALVE

FIELD OF THE INVENTION

The present invention relates to prosthetic heart valves, and in particular to prosthetic heart valves that are combined with an integral vascular graft for use in replacing a diseased aortic valve and a portion of the aorta of a patient.

BACKGROUND OF THE INVENTION

In the normal human heart, illustrated in FIG. 1, deoxygenated blood flows into the right atrium through the superior vena cava and the inferior vena cava. The atrium contracts, allowing blood to flow into the right ventricle. When the ventricle contracts, the deoxygenated blood is pumped through the pulmonary artery to the lungs. Oxygenated blood returning from the lungs enters the left atrium. From the left atrium, the oxygenated blood flows into the left ventricle, which in turn pumps oxygenated blood to the body via the aorta and the lesser arteries.

This pumping action is repeated in a rhythmic cardiac cycle in which the ventricular chambers alternately contract and pump, then relax and fill. As best seen in FIG. 1, a series of one-way cardiac valves prevent backflow of the blood as it moves through the heart and the circulatory system. Between the atrial and ventricular chambers in the right and left sides of the heart are the tricuspid valve and the mitral valve, respectively. At the exits of the right and left ventricles are the pulmonic and aortic valves, respectively.

It is well known that various heart diseases may result in disorders of the cardiac valves. For example, diseases such as rheumatic fever can cause the shrinking or pulling apart of the valve orifice, while other diseases may result in endocarditis, an inflammation of the endocardium or lining membrane of the heart. The resulting defects in the valves hinder the normal functioning of the atrioventricular orifices and operation of the heart. More specifically, defects such as the narrowing of the valve opening, referred to as valvular stenosis, the defective closing of the valve, referred to as valvular insufficiency, result in an accumulation of blood in a heart cavity or regurgitation of blood past the valve. If uncorrected, prolonged valvular stenosis or insufficiency can cause damage to the heart muscle, which may eventually necessitate total valve replacement.

These defects may be associated with any of the cardiac valves, although they occur most commonly in the left heart. For example, if the aortic valve between the left ventricle and the aorta narrows, blood will accumulate in the left ventricle. Similarly, in the case of aortic valve insufficiency, the aortic valve does not close completely, and blood in the aorta flows back past the closed aortic valve and into the left ventricle when the ventricle relaxes.

In many cases, complete valve replacement is required. Mechanical artificial heart valves for humans are frequently fabricated from titanium, pyrolitic carbon or biologic tissue, including tissue from cows, pigs or humans. The more successful artificial heart valves are notable for their non-thrombogenic properties, i.e. their relatively low tendency to cause blood clots. Moreover, they are lightweight, hard and quite strong. Therefore, such valves have become widely accepted and used by many surgeons.

Mechanical prosthetic heart valves typically comprise a rigid orifice supporting one, two or three rigid occluders, or leaflets. The occluders pivot between open and shut positions and thereby control the flow of blood through the valve. The orifice and occluders are commonly formed of pyrolytic carbon, which is a particularly hard and wear resistant form of carbon. Because pyrolytic carbon is relatively brittle, the orifice is often surrounded by a stiffening ring, which may be made of titanium, cobalt chromium, or stainless steel. In one preferred valve configuration, the orifice and stiffening ring are captured within a knit fabric sewing or suture cuff. This prosthetic valve is placed into the valve opening and the sewing cuff is sutured to the patient's tissue. Over time, tissue grows into the fabric of the cuff, providing a secure seal for the prosthetic valve.

It has been found that the efficiency of a prosthetic heart valve is most dependent on the size of the valve opening. In other words, improved characteristics can be expected if the opening of the heart valve is made as large as possible with respect to the patient's anatomy. To accomplish this goal, the valve assembly should be made as radially thin as possible. In the past, some heart valves have been made with three metallic components that surround the orifice and leaflets: a central stiffening ring and upper and lower capture rings to capture the knit fabric tube of the sewing cuff. To hold the upper and lower rings in position, the stiffening ring has frequently been formed with grooves around its inside diameter, which serve to retain the capture rings against an outer side of heart valve annular body. This increases the radial bulk of the valve, however.

Furthermore, in many patients, once degeneration of a valve has occurred, it may occur that surrounding blood vessels are also diseased. Particularly in the case of the aortic valve, surgeons have found that the portion of the aorta adjacent to the valve is often degenerated to the degree that it must be replaced. Consequently, both the aortic valve and a segment of the ascending aorta may be replaced at the same time. This concept is illustrated in FIG. 2 and is described in detail in U.S. Pat. No. 5,123,919, which is hereby incorporated by reference. When this technique was being developed, the surgeon would stitch a segment of vascular graft to the sewing ring of the mechanical valve after implanting the mechanical heart valve. The juncture between the valve and the graft was abrupt and there was usually a sharp change of diameter to be expected between the valve and the graft.

Subsequently, a valve having a preattached graft was developed. The graft is typically attached inside the sewing ring. A major drawback of this configuration is that the valve size has to be reduced in order to accommodate the additional bulk of the graft end. Hence, the valve implanted with this combination is generally smaller than that which a surgeon would ordinarily implant. For example, a surgeon might be forced to implant a 25 mm valve when using an aortic valve/graft combination, when the tissue opening would otherwise suggest using a 27 mm valve. This results in a restriction in the available flow area, with associated resistance to flow. Furthermore, the orifice area (pressure drop across the valve) is proportional to the fourth order power of the internal diameter of the valve. Hence even the slightest diminution of the internal diameter is highly undesirable in the context of heart valve, as it greatly reduces the volume of blood that can be pumped with the available heart muscle.

With the foregoing in mind, it is an objective of the invention to provide a combined mechanical heart valve and graft which has an expanded valve orifice, corresponding to the diameter of the associated graft and tissue opening.

Another object of the invention is to produce a combined heart valve and attached graft wherein the graft is attached to the heart valve adjacent to the end of the sewing cuff so as to minimize the radial thickness of the combination.

SUMMARY OF OUR INVENTION

The present invention provides a combined mechanical heart valve and graft having an expanded valve orifice, corresponding to the diameter of the associated graft and tissue opening. The present invention further provides a combined heart valve and attached graft wherein the graft is attached to the heart valve adjacent to the end of the sewing cuff so as to minimize the radial thickness of the combination. More specifically, the graft end overlaps the downstream end of the sewing cuff and is retained by engagement of a graft retaining ring that engages the downstream sewing cuff retaining ring.

The present mechanical valve comprises a rigid circular orifice supporting internal leaflets. A preferred embodiment comprises a bileaflet valve, but a single leaflet or trileaflet valve could also be used. A optional stiffening ring surrounds the orifice and provides support for a sewing ring to attach the valve to the heart. The retaining ring for the graft and the two retaining rings for the sewing cuff are all outside the stiffening ring.

According to a preferred embodiment, an implantable prosthetic device comprises a valve body, a fabric collar surrounding the valve body having an upstream collar end and a downstream collar end, and a tubular vascular having a proximal graft end and a distal graft end. The proximal end of the graft passes between the fabric collar and the orifice and is retained by mechanical engagement with the fabric collar.

According to another preferred embodiment, an implantable prosthetic valve comprises a valve body including an orifice and a stiffening ring affixed to the orifice, the stiffening ring having an upstream edge, a downstream edge, and an outside diameter, a fabric collar surrounding the valve body; and a tubular vascular graft having a proximal graft end and a distal graft end. The proximal graft end passes between said fabric collar and the orifice but not between the stiffening ring and the orifice.

Still another embodiment of the present invention comprises a method for assembling a mechanical heart valve, comprising providing a valve body, providing a fabric collar having upstream and downstream collar ends, providing a vascular graft having proximal and distal graft ends, placing the proximal graft end inside the downstream collar end, placing the proximal graft end and the downstream collar end around the valve body, and securing the collar to the valve body.

BRIEF DESCRIPTION OF THE DRAWINGS

Other objects and advantages of the invention will become apparent upon reading the following detailed description and upon reference to the accompanying drawings in which.

DETAILED DESCRIPTION OF THE PREFERRED EMBODIMENTS

Figure 1:
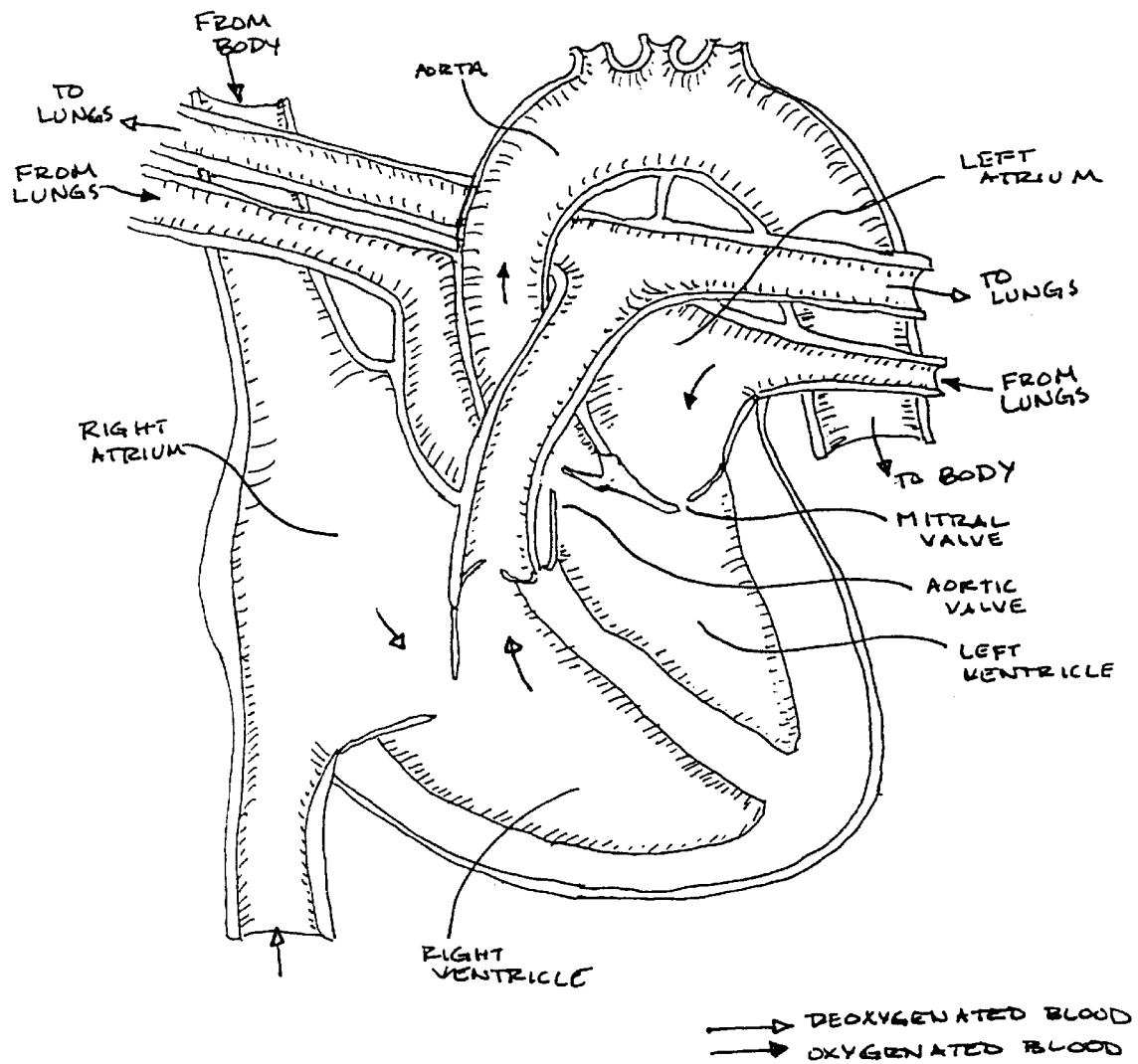
FIG. 1 is a cross-sectional view of a human heart, showing the chambers and valves thereof and the flow of deoxygenated and oxygenated blood therethrough.
Figure 2:
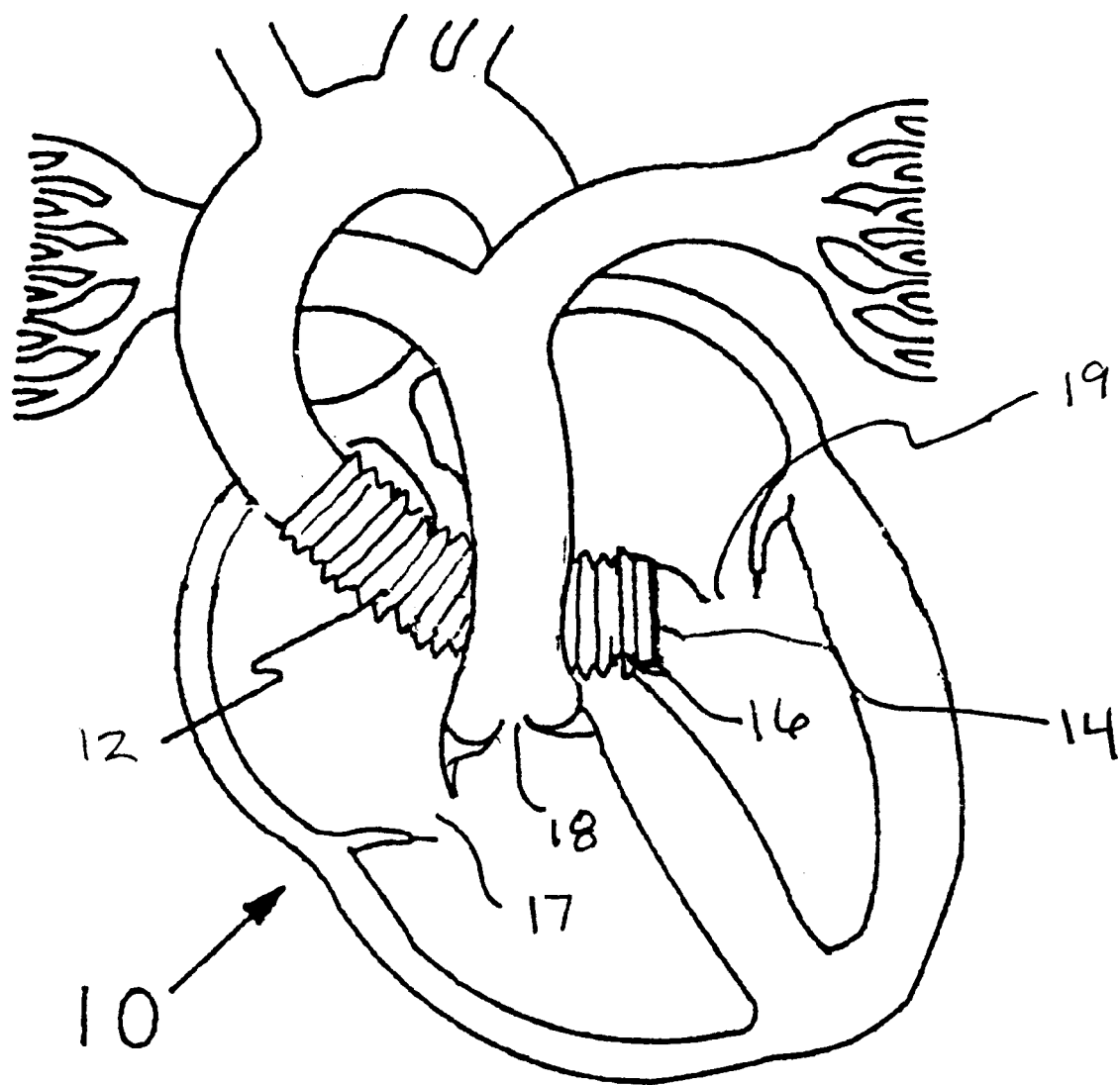
FIG. 2 is a cross-sectional view of a human heart, showing a combined mechanical heart valve and vascular graft according to our invention.

Referring initially to FIG. 2, illustrated is a simplified cross-sectional view of a human heart 10 with a combined mechanical heart valve 14 and graft 12 according to the present invention implanted in place of the aortic valve and a portion of the ascending aorta. For comparison, the natural tricuspid valve 17, pulmonic valve 18 and mitral valve 19 are also shown.

Figure 3:
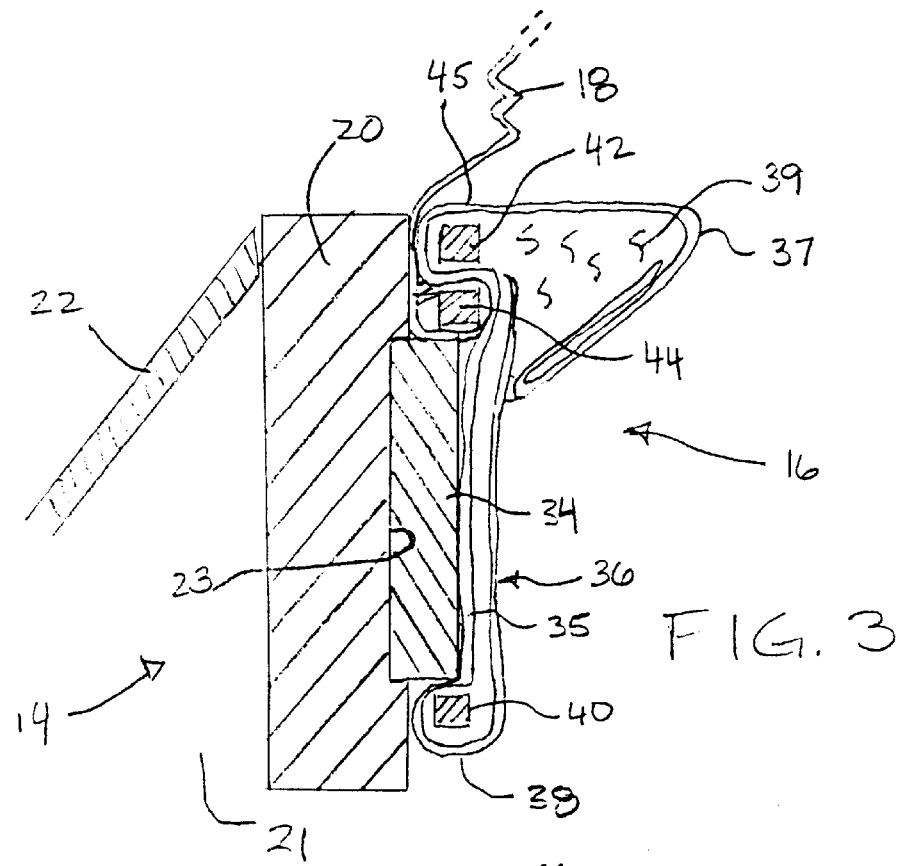
FIG. 3 is an enlarged cross-sectional view of a portion of a preferred embodiment of the combined valve and graft according to the present invention.

The assembly of the combined valve and graft in accordance with the present invention are more clearly shown in FIG. 3. As shown, mechanical valve 14 comprises an orifice 20 having an opening 21 across which lie leaflets 22. The leaflets 22, pivot between open and shut positions about pivots (not shown). Although the invention is illustrated in conjunction with a bileaflet mechanical valve, it will be understood that various other annular mechanical valves can be used in the present invention. As is known in the art, there are typically two pivots for each leaflet, with each pivot diametrically opposed to another across the opening 21. As is also known in this art, additional conventional features may be provided, such as steps to limit rotation of the leaflets.

Surrounding the orifice, a sewing ring assembly 16 may include a stiffening ring 34, fabric sewing collar 36 and first, second and third retaining rings 40, 42, 44 respectively. Because the orifice and leaflets are preferably formed of pyrolitic carbon, which is hard and wear-resistant but relatively brittle, stiffening ring 34 is usually a rigid metal, such as cobalt-chromium or titanium alloys. Fabric collar 36 comprises multiple folds of cloth, which are folded so as to form a toroidal shape that includes an inside layer 35 and an outside layer that includes a suture lip 37. If desired, a filler 39 such as texturized yarn, TEFLON (a trademark) felt, or molded silicon can be captured within the upper end lip 37. The upstream edge 38 of fabric collar 36 is stitched to first retaining ring 40. Similarly, the downstream edge 45 of fabric collar 36, is stitched to second retaining ring 42. The distance between first and second retaining rings 40, 42, which is limited by the shortest length of fabric between rings 40, 42, is preferably greater than the height of stiffening ring 34 and less than the height of orifice 20.

Figure 4:
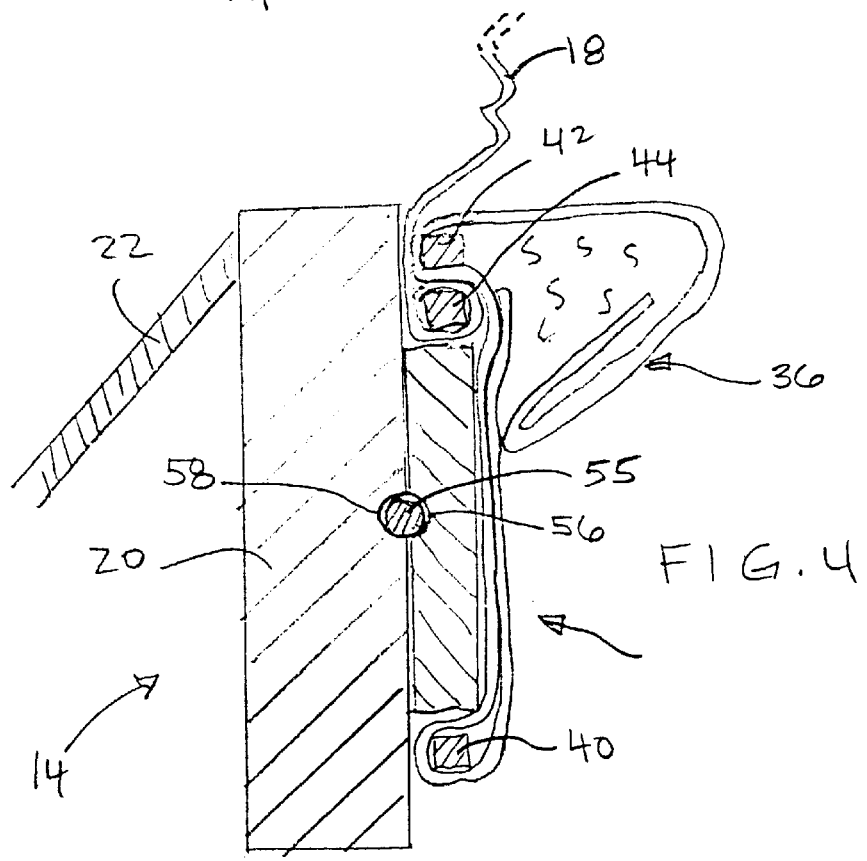
FIG. 4 is an enlarged cross-sectional view of a portion of an alternative embodiment of the combined valve and graft according to the present invention.

According to one preferred embodiment, orifice 20 can be provided with an annular channel 23 in its outer surface. Channel 23 is sized to receive and retain stiffening ring 34 and preferably has a depth that is less than the radial thickness of stiffening ring 34. Because first and second retaining rings 40, 42 are prevented from moving apart by their attachment to fabric collar 36, fabric collar 36 is retained on orifice 20 by engagement of the rings 40, 42 with the upstream and downstream edges of stiffening ring 34. This configuration is preferred, as it provides a minimal radial thickness for the assembled valve and thus allows the largest possible valve opening. Alternatively, and as shown in FIG. 4, orifice 20 can be secured within the sewing ring assembly 16 by an interference ring or lock wire 55, which rests in opposed grooves 56, 58 in stiffening ring 34 and orifice 20 respectively. In this embodiment, fabric collar 36 is again retained on orifice 20 by engagement of the rings 40, 42 with stiffening ring 34. It will be understood that in either instance, the valve, including fabric collar 36 and first and second retaining rings 40, 42, is assembled using known assembly techniques, which include hand-stitching the retaining rings into place.

Alternative structures for connecting an orifice and stiffening ring include a stiffening ring that is press-fit onto the orifice and a stiffening ring that is retained on the orifice by a ridge or lip. Still other alternative structures include no stiffening ring and include instead a ridge, lip or shoulder on the outer surface of the orifice, which ridge, lip or shoulder can serve to engage and retain the fabric collar. The present invention is equally applicable to all of the foregoing configurations.

According to the present invention, and as shown in FIGS. 3 and 4, the proximal or upstream end of graft 12 is affixed, as by stitching, to the third retaining ring 44. In order to attach the graft to the valve body, the upstream end vascular graft 12 passes between orifice 20 and the downstream end of fabric collar 36. The upstream end of vascular graft 12 may be retained by mechanical engagement alone, or may be affixed to fabric collar 36, as by stitching. Retaining ring 44 is positioned between first and second retaining rings 40, 42, and more specifically, between second retaining ring 42 and the downstream edge of stiffening ring 34. This can be accomplished by passing ring 44 through ring 42 before ring 42 is stitched into place on collar 36. Once ring 44 has been positioned on orifice 20, ring 42 slides along the outside of graft 12 until it lies adjacent to ring 44. Ring 42 is then stitched into place. It will be understood that references to "stitching" herein include to the hand-stitching that is conventionally used for such applications and any other attachment technique presently known or hereafter developed.

Because graft retaining ring 44 has an outside diameter that is larger than the inside diameter of retaining ring 42, mechanical engagement of ring 44 with ring 42 retains the graft on the valve. The same mechanical engagement between the proximal end of the graft and the fabric collar can be achieved by providing a ridge, pleat, or similar device to the proximal graft end. The ridge, pleat or similar device would engage the fabric collar in the same manner as does graft retaining ring 44. Similarly, should it be desired to manufacture fabric collar 36 without retaining ring 42, mechanical engagement with the graft can be achieved by similar means.

It will be understood from the foregoing that the present invention can be used to retain a graft on a prosthetic valve, regardless of whether the valve includes a stiffening ring, and regardless of how the fabric suture cuff is affixed to the valve.

The present invention reduces the total radial thickness of the valve with attached graft and so allows a larger valve to be used than was previously possible. Furthermore, the present invention retains the graft solidly in place and can be used with existing valve stock, as the graft is retained by engagement with the fabric cuff and thus does not require any modification of the other components of the valve.

The invention may be embodied in other specific forms without departing from the spirit or essential characteristics thereof. The invention therefore, is to be defined by the appended claims, and not by the foregoing description. All variations that come within the meaning and doctrine of equivalency of claims are therefore intended to be included therein.

What is claimed is:

1. An implantable prosthetic heart valve comprising:
   a valve body comprising an orifice member;
   a stiffening member coupled to the orifice member, said stiffening member having upstream and downstream edges;
   a fabric collar;
   a first collar retaining ring coupling the fabric collar to the orifice member, said first collar retaining ring being downstream of said downstream edge of said stiffening member;
   a tubular vascular graft having a proximal graft end; and
   a graft retaining ring coupling the tubular vascular graft to the orifice member, said graft retaining ring being downstream of said downstream edge of said stiffening member and upstream from said first collar retaining ring, wherein the graft retaining ring is coupled to said proximal graft end and is coupled to the orifice member by mechanical engagement between said first collar retaining ring and the downstream edge of the stiffening member.

2. The heart valve according to claim 1 wherein the fabric collar further comprises upstream and downstream collar ends.

3. The heart valve according to claim 2, wherein said first collar retaining ring is coupled to said downstream collar end, and further comprising a second collar retaining ring coupled to said upstream collar end.

4. The heart valve according to claim 1, further comprising a lock wire.

5. The heart valve according to claim 4 wherein the stiffening member includes a groove formed therein for receiving the lock wire.

6. The heart valve according to claim 4 wherein the orifice member includes a groove formed therein for receiving the lock wire.

7. The heart valve according to claim 4 wherein the stiffening member and the orifice member each include a groove for receiving the lock wire.

8. The device according to claim 1 wherein said stiffening member is affixed to said orifice member by engagement with a channel in said valve body, said channel being sized and configured to receive and retain said stiffening member.

9. The device according to claim 1 wherein said stiffening member is coupled to said orifice member by a locking ring that rests in opposed grooves in an outside surface of said orifice member and an inside surface of said stiffening member.

10. An implantable prosthetic device comprising:
    a valve body including an orifice member;
    a stiffening member coupled to the orifice member;
    a fabric collar coupled to the orifice member;
    at least one fabric collar retaining ring coupled to the orifice member, the fabric collar retaining ring having an inside diameter;
    a graft retaining ring engaged annularly between the fabric collar retaining ring and the stiffening member, the graft retaining ring having an outside diameter which is greater than the inside diameter of the fabric collar retaining ring; and
    a tubular vascular graft having a proximal graft end coupled to said graft retaining ring, the graft end being coupled to the valve body by the engagement of the graft retaining ring and the fabric collar retaining ring.

11. The device according to claim 10, further comprising a lock wire.

12. The device according to claim 10 wherein the fabric collar comprises upstream and downstream collar ends, further comprising a first fabric collar retaining ring attached to the upstream collar end and a second fabric collar retaining ring attached to the downstream collar end.

13. The device according to claim 11 wherein the stiffening member includes a groove formed therein for receiving the lock wire.

14. The device according to claim 11 wherein the orifice member includes a groove formed therein for receiving the lock wire.

15. The device according to claim 11 wherein the stiffening member and the orifice member each include a groove formed therein for receiving the lock wire.

16. A method for assembling a mechanical heart valve comprising:
   (a) providing a valve body comprising an orifice member;
   (b) providing a stiffening member, said stiffening member having upstream and downstream edges coupled to the orifice member;
   (c) providing a fabric collar comprising at least one fabric collar retaining ring;
   (d) coupling one of said at least one fabric collar retaining rings to the valve body;
   (e) providing a graft retaining ring downstream of said downstream edge of said stiffening member and engaging said graft retaining ring annularly between said at least one fabric collar retaining ring and said stiffening member; and
   (f) providing a tubular vascular graft coupled to the graft retaining ring and having a proximal graft end, the graft end being retained on the valve body by the engagement of the graft retaining end and said one of said at least one fabric collar retaining rings.

17. The method according to claim 16, further including the step of affixing the stiffening member to the valve body by providing a lock wire that engages opposed grooves in an inner surface of the stiffening member and an outer surface of the orifice member.

18. The method according to claim 16, further including the step of providing a first and a second fabric collar retaining ring.

19. An implantable prosthetic heart valve comprising
   a valve body comprising an orifice member;
   a sewing collar coupled to the orifice member, said sewing collar comprising an upstream collar end and a downstream collar end;
   a sewing collar retaining ring coupled to said downstream collar end;
   a tubular vascular graft having a proximal graft end and a distal graft end; and
   a graft retaining ring coupled to said proximal graft end, wherein said graft retaining ring is annularly disposed around the orifice member and inside the sewing collar between the upstream and downstream collar ends, and wherein said graft is retained on said orifice member in a downstream direction solely by mechanical engagement of said graft retaining ring and said sewing collar retaining ring at said downstream collar end.

* * * * *